United States Patent
Yobas et al.

(10) Patent No.: US 9,937,498 B2
(45) Date of Patent: Apr. 10, 2018

(54) ARTIFICIAL SIEVING STRUCTURES

(71) Applicant: The Hong Kong University of Science and Technology, Hong Kong (CN)

(72) Inventors: Levent Yobas, Hong Kong (CN); Zhen Cao, Hong Kong (CN)

(73) Assignee: THE HONG KONG UNIVERSITY OF SCIENCE AND TECHNOLOGY, Kowloon (HK)

( * ) Notice: Subject to any disclaimer, the term of this patent is extended or adjusted under 35 U.S.C. 154(b) by 218 days.

(21) Appl. No.: 14/706,356

(22) Filed: May 7, 2015

(65) Prior Publication Data

US 2015/0323499 A1  Nov. 12, 2015

Related U.S. Application Data

(60) Provisional application No. 61/996,497, filed on May 9, 2014.

(51) Int. Cl.
*G01N 27/447* (2006.01)
*B01L 3/00* (2006.01)

(52) U.S. Cl.
CPC ..... *B01L 3/502746* (2013.01); *B01L 3/50273* (2013.01); *B01L 3/502707* (2013.01);
(Continued)

(58) Field of Classification Search
CPC ........... B01L 3/502746; B01L 3/50273; B01L 3/502707; B01L 3/502761;
(Continued)

(56) References Cited

U.S. PATENT DOCUMENTS 6,685,810 B2   2/2004  Noca et al.
6,753,200 B2   6/2004  Craighead et al.
(Continued)

OTHER PUBLICATIONS

Cao, et al. "Monolithic integration of fine cylindrical glass microcapillaries on silicon for electrophoretic separation of biomolecules" Biomicrofluidics, vol. 6, No. 3, Sep. 2012, p. 036501-1-036501-11.*

(Continued)

*Primary Examiner* — J. Christopher Ball
(74) *Attorney, Agent, or Firm* — Pillsbury Winthrop Shaw Pittman LLP

(57) ABSTRACT

Disclosed herein is a device for electrophoresis comprising: a separation channel in a substrate; and a plurality of capillary-well motifs cascading along the separation channel, each of the plurality of capillary-well motifs comprising a well and a plurality of non-intersecting capillaries, wherein the capillaries are downstream from the well and fluidly connected thereto, an interface between the well and the capillaries comprises a step profile. Also disclosed is a method comprising: obtaining a substrate comprising an insulator layer of an insulator material; forming a well and a plurality of trenches in the insulator layer so that only the insulator material is exposed to an interior of the well and the plurality of trenches; nonconformally depositing a film into the plurality of trenches until the film pinches off top openings of the trenches and forms a tubular void therein; transforming the tubular void into a capillary by annealing the film.

25 Claims, 22 Drawing Sheets

(52) U.S. Cl.
CPC .. B01L 3/502761 (2013.01); G01N 27/44791 (2013.01); B01L 2200/12 (2013.01); B01L 2300/0816 (2013.01); B01L 2300/0838 (2013.01); B01L 2300/0896 (2013.01); B01L 2300/12 (2013.01); B01L 2400/0421 (2013.01); B01L 2400/086 (2013.01)

(58) Field of Classification Search
CPC ....... B01L 2400/0421; B01L 2400/086; B01L 2300/0816; B01L 2300/12; B01L 2300/0896; B01L 2300/0838; B01L 2200/12; G01N 27/44791
See application file for complete search history.

(56) References Cited

U.S. PATENT DOCUMENTS

| 7,918,979 B2 | 4/2011 | Han et al. |
| 2007/0090026 A1 | 4/2007 | Han et al. |

OTHER PUBLICATIONS

Han, et al "Entropic trapping and sieving of long DNA molecules in a nanofluidic channel" Journal of Vacuum Science and Technology A, vol. 17, No. 4, Jul./Aug. 1999, p. 2142-2147.*

H. Cao, et al "Gradient nanostructures for interfacing microfluidics and nanofluidics" Applied Physics Letters, vol. 81, No. 16, Oct. 2002, p. 3058-3060.*

W. D. Volkmuth et al., "DNA electrophoresis in microlithographic arrays", Letters to Nature, Department of Physics, Princeton University, Princeton, New Jersey, vol. 358, Aug. 13, 1992.

Noritada Kaji et al., "Separation of Long DNA Molecules by Quartz Nanopillar Chips under a Direct Current Electric Field", Anal. Chem. 2004, 76, 15-22.

J. Han et al., "Separation of Long DNA Molecules in a Microfabricated Entropic Trap Array", Science 288, 1026 (2000).

J. Han et al., "Entropic Trapping and Escape of Long DNA Molecules at Submicron Size Constriction", Physical Review Letters, vol. 83, No. 8, Aug. 23, 1999.

Jongyoon Han et al., "Characterization and Optimization of an Entropic Trap for DNA Separation", Anal. Chem. 2002, 74, 394-401.

Jianping Fu et al., "Nanofilter array chip for fast gel-free biomolecule separation", Applied Physics Letters 87, 263902 (2005).

Jianping Fu et al., "Molecular Sieving in Periodic Free-Energy Landscapes Created by Patterned Nanofilter Arrays", Physical Review Letters, PRL 97, 018103 (2006).

Yong Zeng et al., "Self-Assembled Colloidal Arrays as Three-Dimensional Nanofluidic Sieves for Separation of Biomolecules on Microchips", Anal. Chem. 2007, 79, 2289-2295.

Patrick S. Doyle et al., Self-Assembled Magnetic Matrices for DNA Separation Chips, Science, vol. 295, Mar. 22, 2002.

* cited by examiner

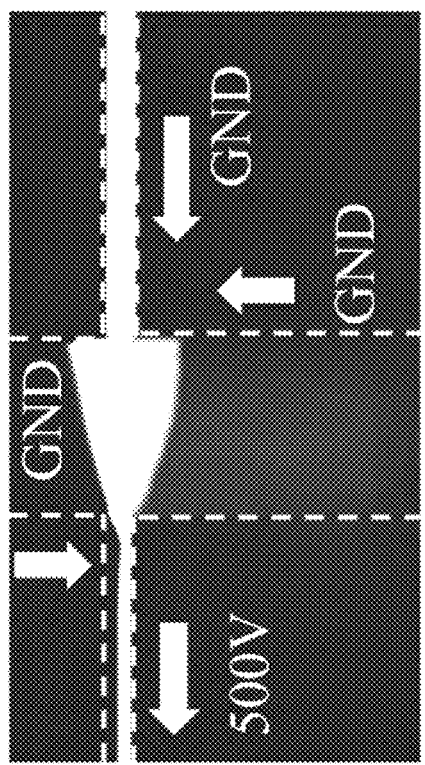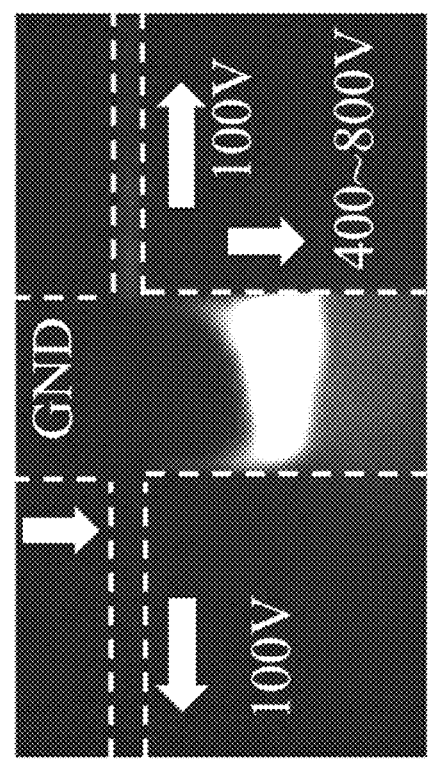
Fig. 3A
Fig. 3B

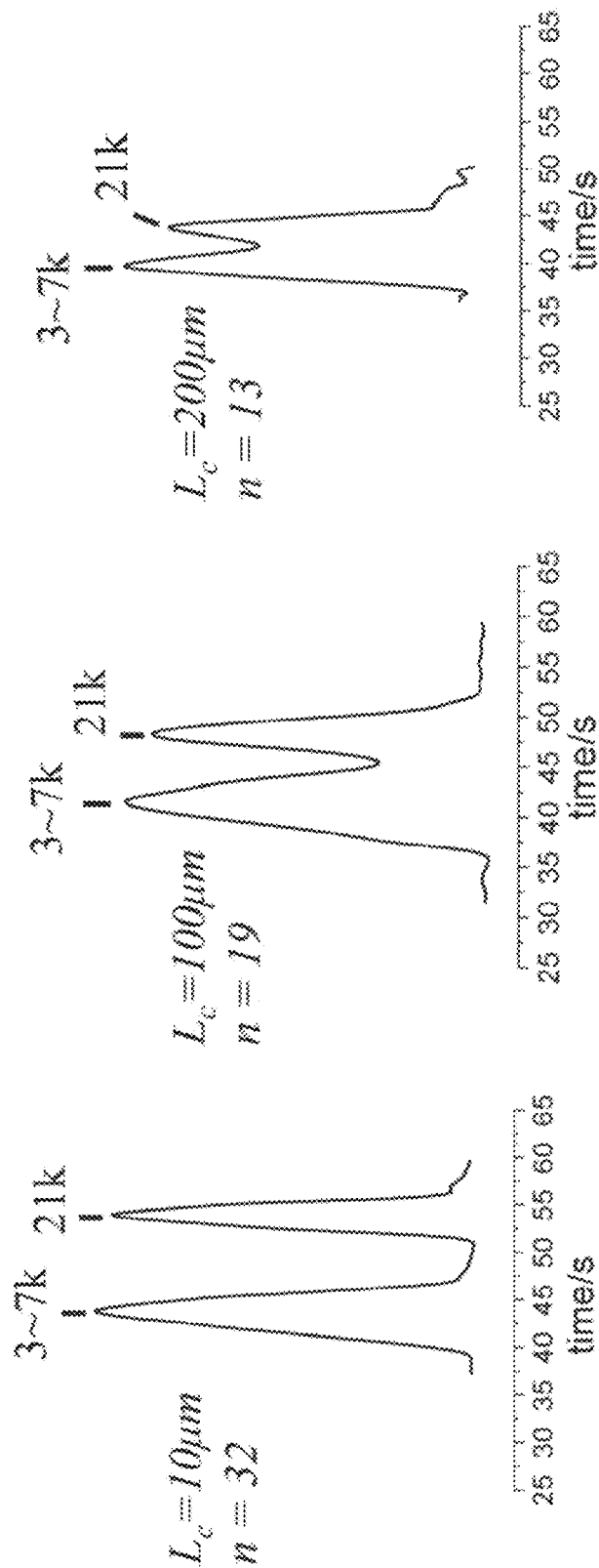

ARTIFICIAL SIEVING STRUCTURES

CROSS-REFERENCE TO RELATED APPLICATIONS

The present application claims priority to U.S. Provisional Patent Application No. 61/996,497, filed on May 9, 2014, which is incorporated herein by reference in its entireties.

BACKGROUND

Artificial sieving structures such as engineered micro/nanostructures may be used for the size-dependent electrophoretic separation of macromolecules in free solution, particularly for DNA and proteins. These structures, given their highly regular topography and precise dimensions, can be a potential substitute for restrictive gelatinous materials (gels) or viscous sieving polymer solutions.

SUMMARY

Disclosed herein is a device for electrophoresis comprising: a separation channel in a substrate; and a plurality of capillary-well motifs cascading along the separation channel, each of the plurality of capillary-well motifs comprising a well and a plurality of non-intersecting capillaries, wherein the capillaries are downstream from the well and fluidly connected thereto, and an interface between the well and the capillaries comprises a step profile.

According to an embodiment, the well has a greater dimension in a direction perpendicular to a flow of the separation channel than that of the capillaries.

According to an embodiment, the capillaries comprise a center section of essentially uniform cross-sectional area.

According to an embodiment, the capillaries comprise fluid access ports with a greater cross-sectional area than the center section.

According to an embodiment, the center section has a width of 1 micron or less.

According to an embodiment, the wells of the plurality of capillary-well motifs are essentially identical in their dimensions.

According to an embodiment, the capillaries of the plurality of capillary-well motifs are essentially identical in their dimensions.

According to an embodiment, the well is positioned perpendicularly to the capillaries.

According to an embodiment, the device further comprises a sample channel and one or more reservoirs.

According to an embodiment, the plurality of capillary-well motifs comprises at least 1, at least 5, or at least 10 capillary-well motifs.

According to an embodiment, the plurality of capillary-well motifs comprises at least 100 capillary-well motifs.

According to an embodiment, the plurality of non-intersecting capillaries comprises 3 or more, 5 or more, or 10 or more capillaries.

According to an embodiment, the plurality of non-intersecting capillaries has a length of 1 microns or more, 5 microns or more, or 10 microns or more. The capillaries may have a length from 30% to 60% of the pitch of the capillary-well motifs.

According to an embodiment, the well has a depth of 3 microns or more.

According to an embodiment, the center section of the capillaries is buried or enclosed.

Disclosed herein is a method of forming a device, the method comprising: obtaining a substrate comprising an insulator layer of an insulator material; forming a plurality of trenches in the insulator layer so that only the insulator material is exposed to an interior of the plurality of trenches; nonconformally depositing a film into the plurality of trenches until the film pinches off top openings of the trenches and forms a tubular void therein; transforming the tubular void into a capillary by annealing the film; and forming a well in the insulator layer so that only the insulator material is exposed to an interior of the well.

According to an embodiment, the method further comprises reducing a size of the capillary by annealing the capillary.

According to an embodiment, the insulator material is an oxide.

According to an embodiment, the substrate is a semiconducting or conducting substrate.

According to an embodiment, the substrate is made of the insulator material.

According to an embodiment, the substrate is a glass or quartz substrate.

According to an embodiment, the insulator material is undoped.

According to an embodiment, the insulator material is silicate glass (USG), spin-on-glass (SOG), low-temperature oxide (LTO), high-temperature oxide (HTO), thermally grown oxide, or oxide based on tetraethylorthosilicate (TEOS).

According to an embodiment, the insulator material has lighter doping than the film.

According to an embodiment, the method further comprises depositing a diffusion barrier.

According to an embodiment, the capillary has a size of 100 nm or less.

According to an embodiment, the film is doped glass.

According to an embodiment, the film is phosphorus-doped glass (PSG) or borophosphosilicate glass (BPSG).

BRIEF DESCRIPTION OF THE DRAWINGS

FIG. 3A and FIG. 3B show fluorescence micrographs showing "pinched" injection of a DNA sample plug into the artificial sieving structure;

FIG. 3C, FIG. 3D and FIG. 3E show electropherograms obtained from three exemplary designs of the artificial sieving structure at the end of 5 mm long separation channels in three distinct devices, where the wells have a depth of 23 microns, a length of 35 microns and a width of 140 microns;

DETAILED DESCRIPTION

Figure 1A:
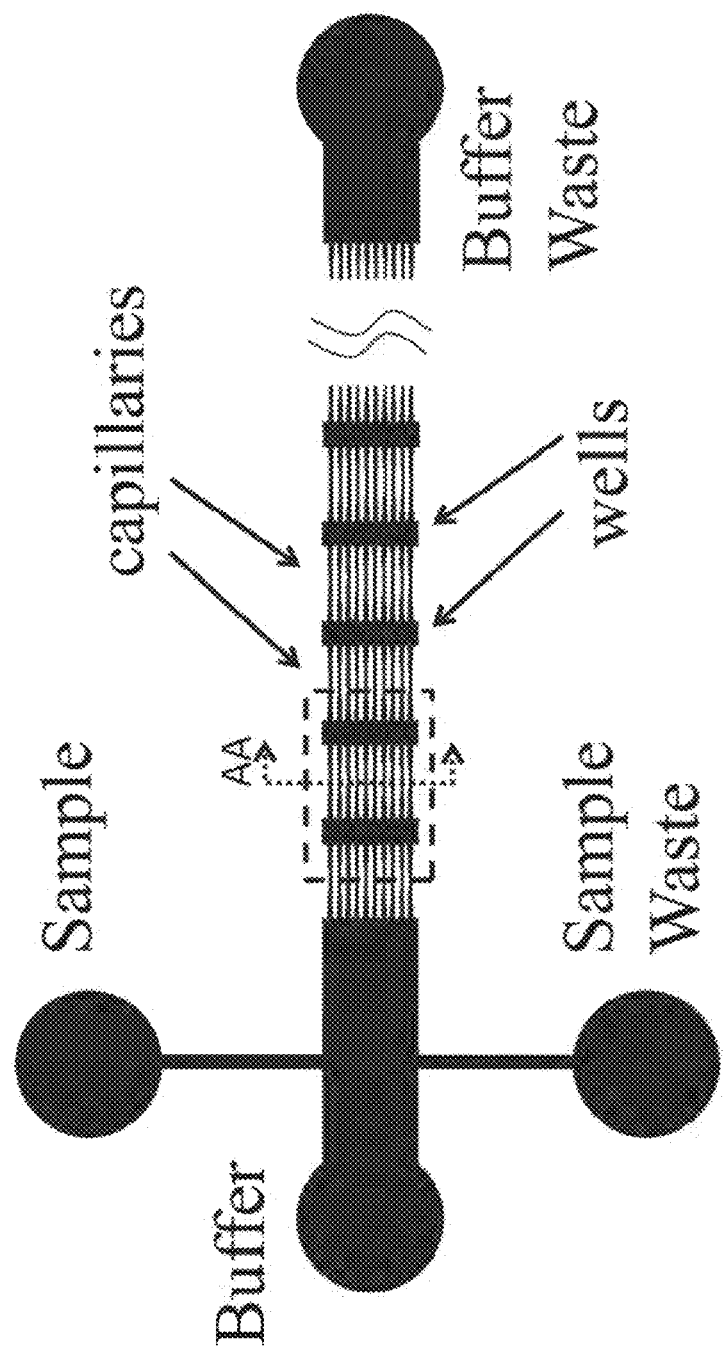
FIG. 1A schematically shows an artificial sieving structure according to an embodiment, including capillary-well motifs arranged along a separation channel integrated with a sample injection cross-junction.

The artificial sieving structures in present teaching are also called artificial gel structures although the artificial sieving structures may not contain any gelatinous materials. The artificial sieving structures may allow separation of DNA molecules greater than 10 kbp under a constant electric field, and thus reduce the need for pulsing or switching the electric field and its associated inefficiency. The artificial sieving structures may present completely new physical effects in probing dynamics of macromolecules. The artificial sieving structures may not have to be freshly prepared before deployment and may not require incorporation into confining spaces. The artificial sieving structures afford more flexibility of system design of microchips and can be fabricated with established semiconductor fabrication techniques. Dimensions of the artificial sieving structures may be precisely controlled and may allow for more rigorous tests for the existing theories and may lead to more insightful models of electrophoresis.

The artificial sieving structures may have confining spaces on a structured planar surface under a coverplate of glass or under soft elastomer directly bonded to the surface. Alternatively, the artificial sieving structures may be a monolithic unit by removing a sacrificial spacer (e.g., polysilicon) between a pair of structural layers (e.g., silicon nitride) placed on a planar substrate (e.g., silicon). The artificial sieving structures may include arrays of micrometer or submicrometer-scale pillars ("post arrays"), asymmetric obstacle courses ("Brownian ratchets"), or microchannels with alternating segments of deep and shallow regions ("slit-well motifs"). The artificial sieving structures may be patterned via optical (contact or projection) or electron-beam (e-beam) lithography and subsequent dry etching. Post arrays may have micrometer-scale gaps (e.g., 1-2 µm) to extend Ogston sieving regime to long molecules. Pulsing the electric field in post arrays with micrometer-scale gaps may be helpful to induce a high-speed separation several orders of magnitude faster than by traditional polymer gels. Post arrays may have submicrometer-scale gaps (e.g., 500 nm or less) and be operated under a constant electric field with Ogston and reptation-like mechanisms. The entropic recoil effect may facilitate separation of long DNA molecules trapped at the interface of a post array with smaller gaps (e.g., 100 nm) and thereby leading to their separation under a pulsed field. Entropic effects may also increase escape and mobility of longer DNA molecules in the slit-well motif.

According to an embodiment, the confining spaces of an artificial sieving structure may be fabricated without using advanced patterning tools (e.g., projection, e-beam, or nanoimprint) or wafer bonding techniques. Such an artificial sieving structure may be made using standard photolithography and dry etching techniques to impart a surface topography with trench features (e.g., >1 µm width), which then serves as a template for precision-molding in-plane near-cylindrical capillaries with a submicrometer diameter. A film (e.g., glass or doped glass) may be nonconformally deposited into the trench features and annealed to cause thermal reflow of the film. The diameter of the capillaries may be adjusted through the annealing step in which capillaries evolve into near-cylindrical tubes and then gradually shrink in diameter while essentially preserving their shape under thermal reflow. The capillaries can be self-enclosed owing to a nonconformal deposition profile of the film. Capillaries may have various lengths such as less than 50 µm, and more than 10 mm. The lengths of the capillaries may be as short as 1 micron. The diameter of the capillaries may be as small as 50 nm.

Figure 1B:
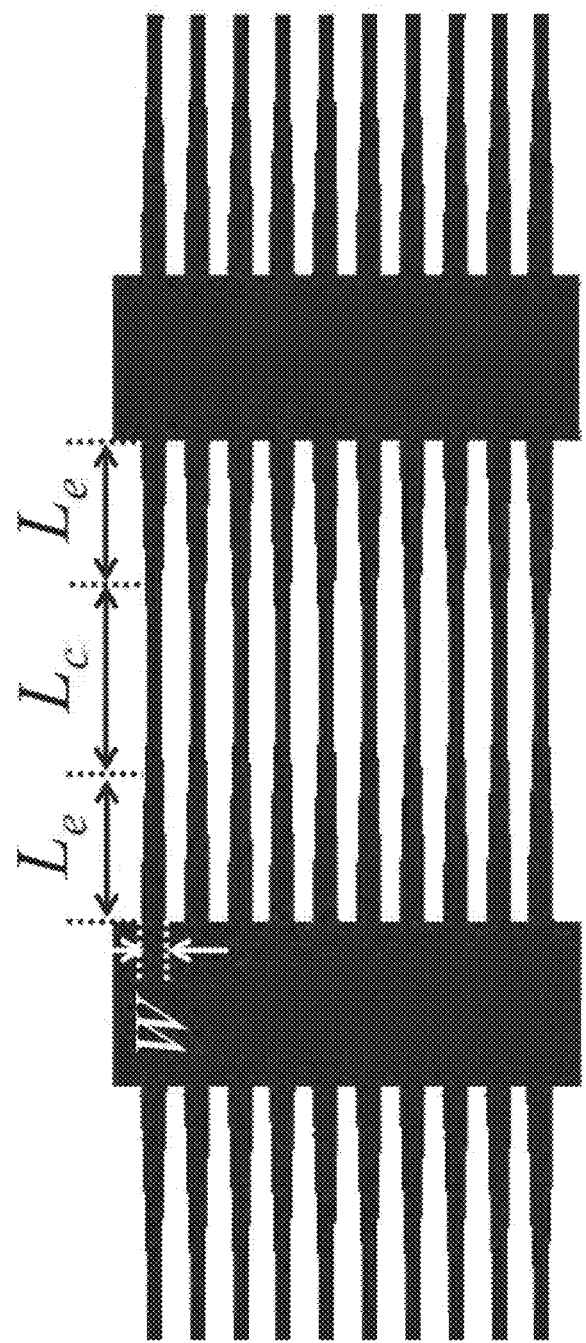
FIG. 1B schematically shows an example of a capillary-well motif including 10 capillaries in parallel and flanked by wells, where the capillaries possess a buried center section of uniform diameter over a length of $L_c$ and then gradually expands and opens up over a length $L_e$ toward one or both of the wells.
Figure 1C:
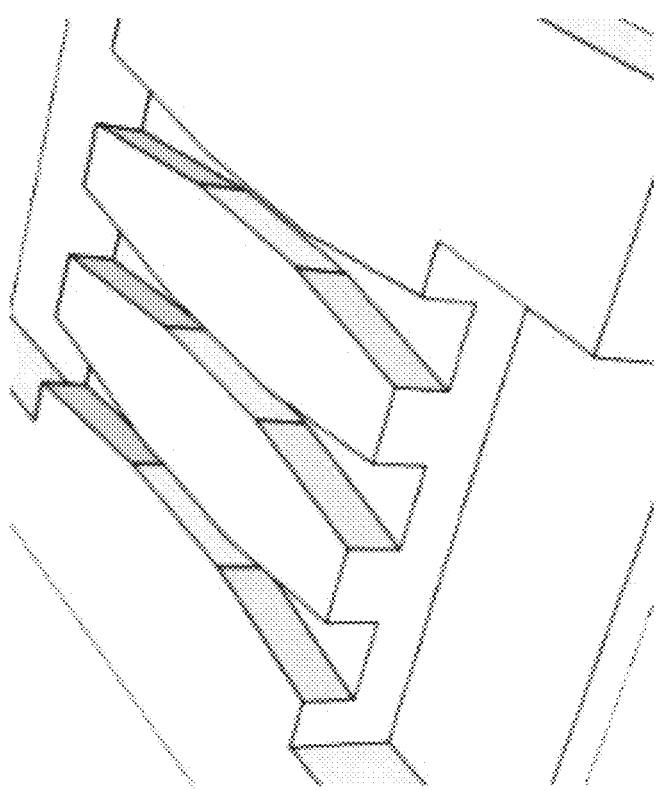
FIG. 1C and FIG. 1D respectively show 3D rendering of the substrate prestructured with a dual-step profile including channels flanked by two wells before and after deposition and thermal reflow of a deposited film (e.g., glass)
Figure 1D:
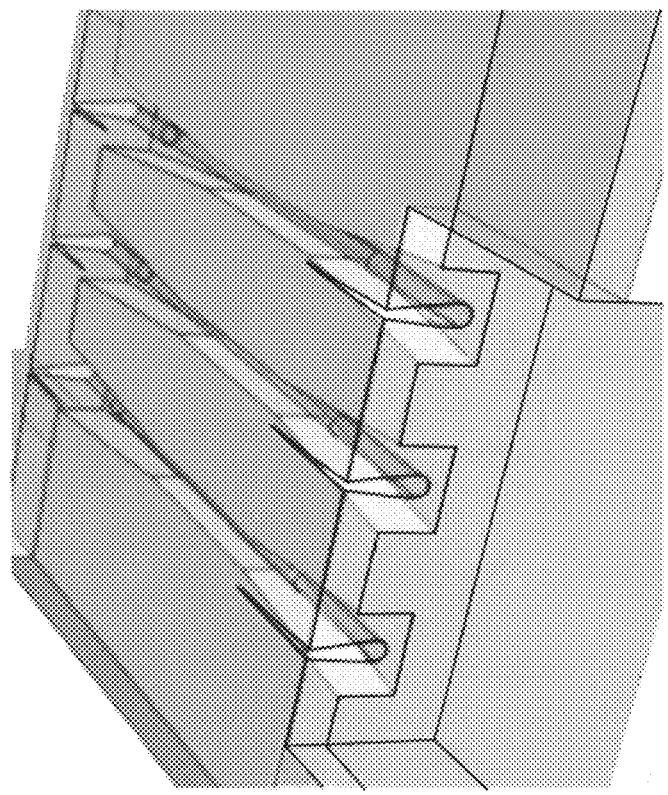

FIG. 1A schematically shows an artificial sieving structure according to an embodiment. This artificial sieving structure has sample injection cross-junction for launching sample (e.g., DNA) plugs into an integrated capillary array of the artificial sieving structure. The capillary array may have a repeated pattern of a capillary-well motif where the capillaries in the motif may be parallel to one another and may have essentially (±5%) the same length and diameter. As shown in FIG. 1B, FIG. 1C and FIG. 1D, the capillaries in the motif may maintain a uniform diameter over a length of $L_c$ and have an enlarged (e.g., conical) fluid access ports over $L_e$ on either or both sides. The enlarged fluid access ports may be made by diverging trench ends in which the capillaries are molded (see FIG. 1B). The spatial gradient profile offered by the enlarged fluid access ports can facilitate long DNA chains (e.g., genomic DNA) to stretch and thus to be more effectively introduced into the capillaries under the applied field. The capillaries do not have to be straight but can be arranged in a winding pattern.

Microfabrication

The capillaries may be fabricated using a method described below. This method is not the only possible method of fabricating the capillaries. Precursor for each capillary may be defined within a trench in a substrate (e.g., silicon) as a self-enclosed void with a cross-sectional profile like a tear drop by nonconformal deposition of a film (e.g., doped glass) into the trench. Reflow of the film during a thermal anneal step may lead to shape transformation as the voids evolved into nearly cylindrical capillaries so as to minimize the free surface energy of the voids. Along with the capillaries, enlarged fluid access ports may also be formed through the same process owing to the diverging ends of the trenches (e.g., with a larger width at one or both open ends of the trenches, for example shown in FIG. 1C and FIG. 1D. The diverging ends of the trenches may eliminate dry etching the film to form access ports to the capillaries. A dual-step profile (i.e., steps at the interfaces of the capillaries and the flanking wells) may be fabricated by a suitable technique such as deep reactive ion etching (DRIE) the substrate initially through a first mask (to form the wells, reservoirs, and the channels for the sample injection junction) and then through a second mask (to form the trenches). The steps at the interfaces of the capillaries and the flanking wells are abrupt height changes. Namely, the depth (dimension in a direction perpendicular to the flow direction) of the wells is greater than the dimension (e.g., diameter) of the capillaries in the same direction. The depth of the wells may be greater than the depth of the trenches. Alternatively, the step at the downstream end of capillaries may not have to be positioned immediately at the egress of the capillaries. After both etching steps, the substrate may be passivated, for example, with a thermally grown 0.7 µm thin-film silicon dioxide. The film (e.g., a layer of 5 µm thick phosphosilicate glass (PSG)) may be then nonconformally deposited using a suitable technique such as low-pressure chemical vapor deposition process (LPCVD, e.g., at 180 mTorr, 420° C.). The voids—the so-called capillary precursors—may transform into nearly cylindrical capillaries due to thermal reflow during a thermal anneal step (e.g., performed at 1000° C. for 1 h). The substrate may be aligned and permanently bonded with a elastomer slab (e.g., poly (dimethylsiloxane) (PDMS; Dow Corning 184)) with inlet/outlet holes after their mating surfaces are activated in oxygen plasma (e.g., at 29.6 W for 45 s, Harrick Plasma).

The trenches may be made in a semiconductor such as silicon or in an insulator such as silicon oxide. In one example, the trenches are made in an insulator layer on a substrate. In one example, the substrate itself is entirely an insulator. Having the trenches in an insulator may help increase the maximum voltage the artificial sieve structure may withstand before electrical breakdown occurs and may eliminate the need to insulate any exposed conducting or semiconducting material after making the wells by etching.

Figure 6A:
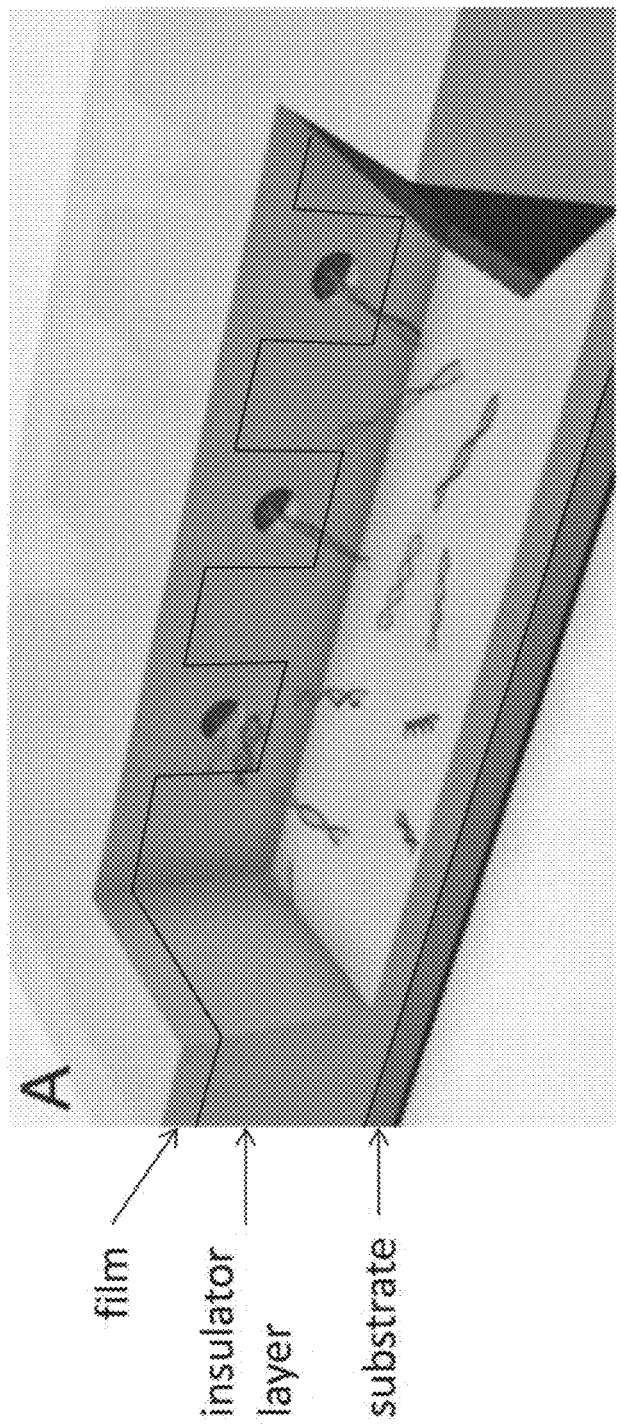
FIG. 6A shows a three-dimensional rendering of an area around the interface between a well and a group of capillaries in a well-capillary motif, according to an embodiment.
Figure 6B:
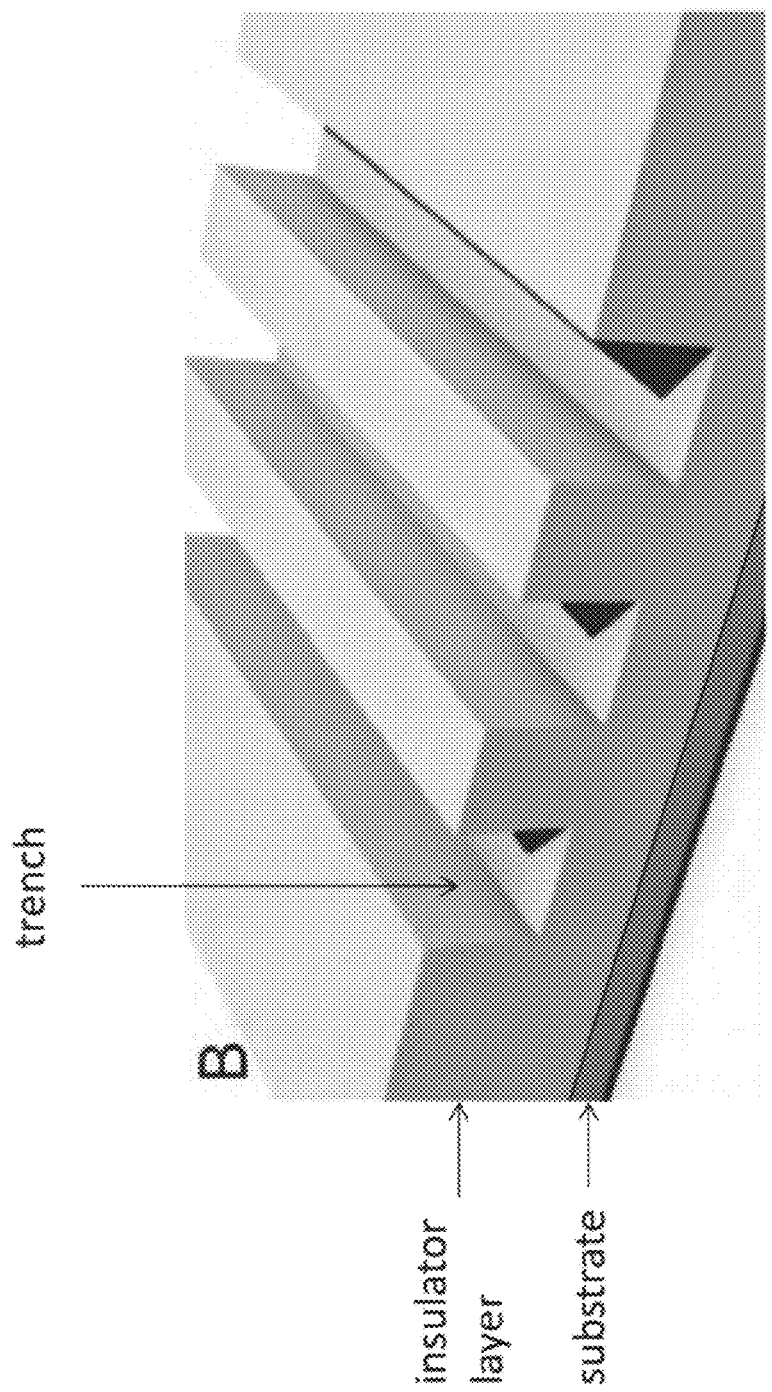
FIG. 6B shows a cross-sectional view of trenches (e.g., with a width greater than 1 micron) are made in an insulator layer, for use as a template for forming the capillaries therein.
Figure 6C:
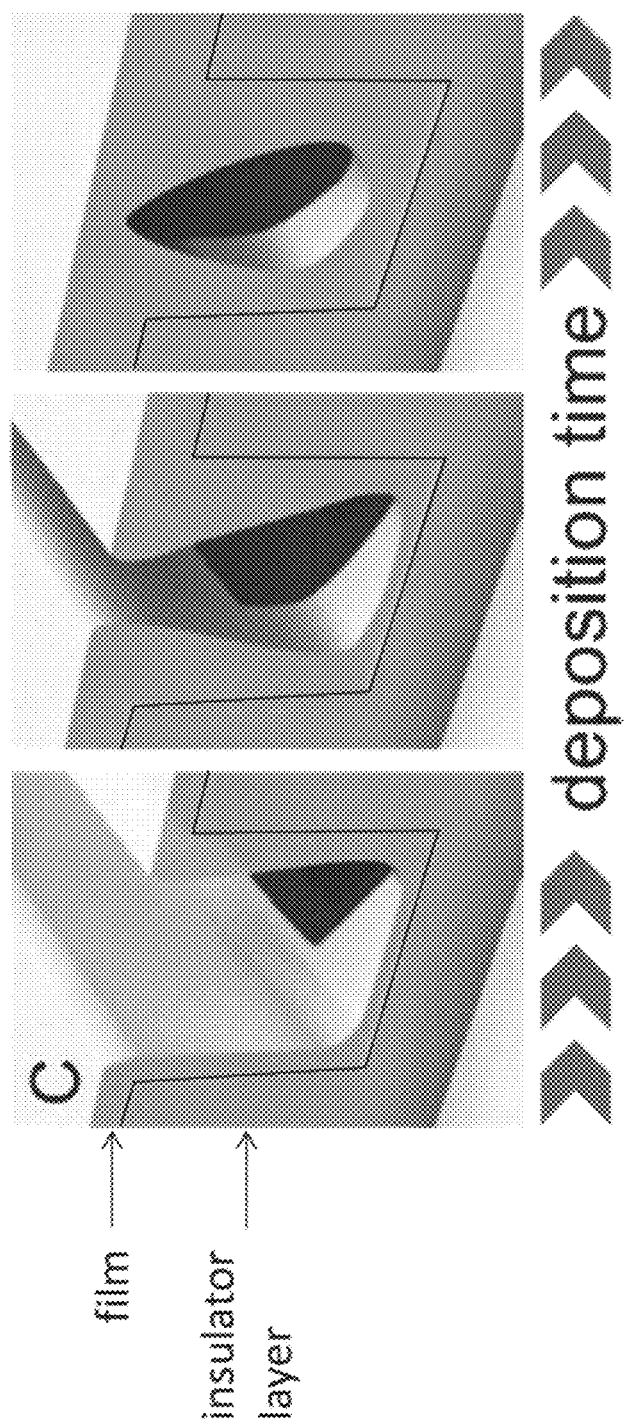
FIG. 6C shows a cross-sectional view of nonconformal deposition of a film (e.g., doped glass) into the trenches.
Figure 6D:
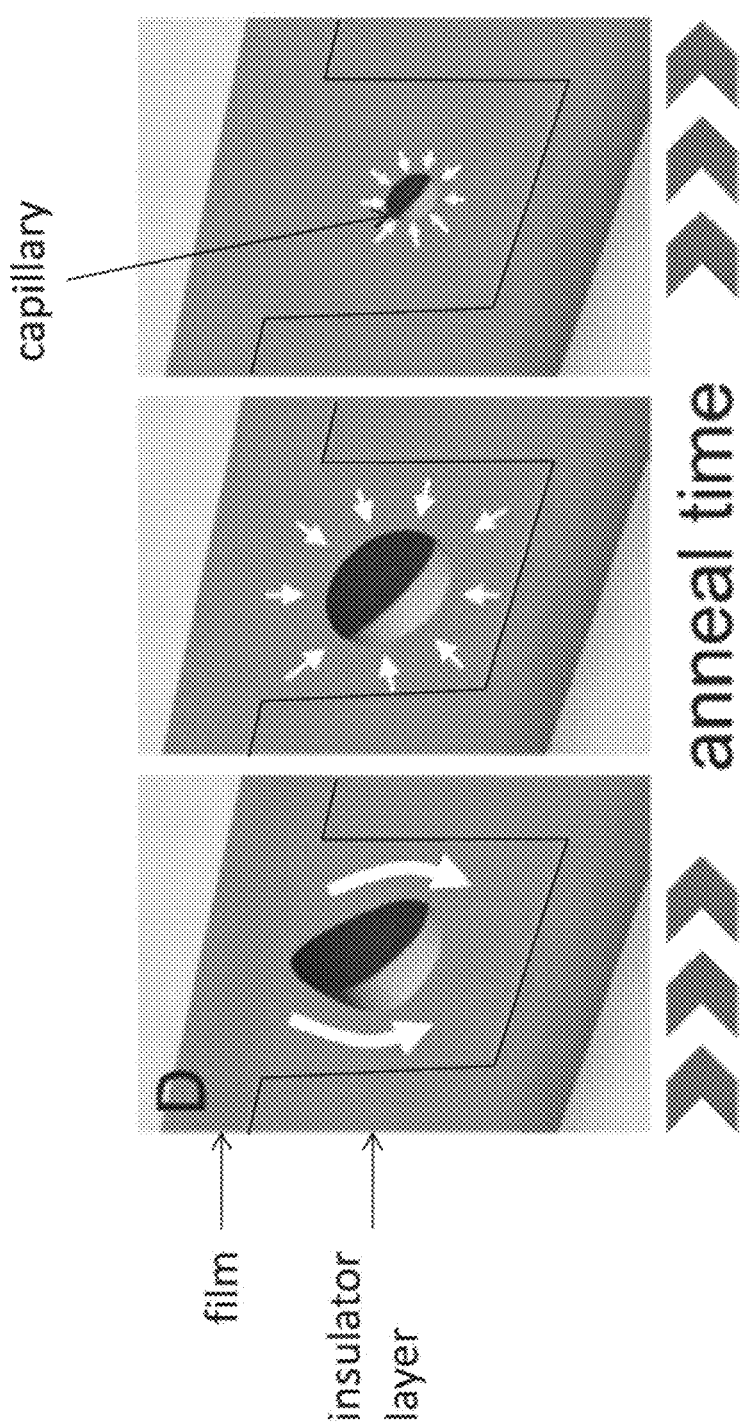
FIG. 6D shows a cross-sectional view of reflow of the film during thermal annealing and as a result the transformation of the tubular void into a capillary.
Figure 7B:
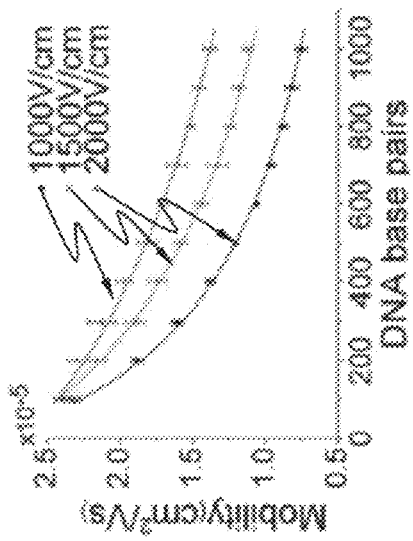
FIG. 7B shows mobilities as a function of DNA fragment sizes of the 100 bp DNA ladder through the artificial sieving structure of FIG. 7A under the three different electric field strengths.
Figure 7C:
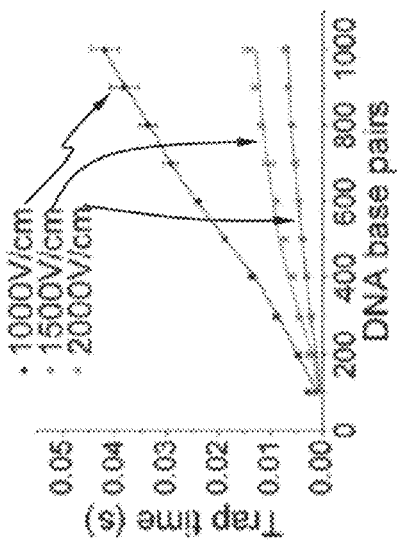
FIG. 7C shows trap times as a function of DNA fragment sizes of the 100 bp DNA ladder through the artificial sieving structure of FIG. 7A under the three different electric field strengths.
Figure 7A:
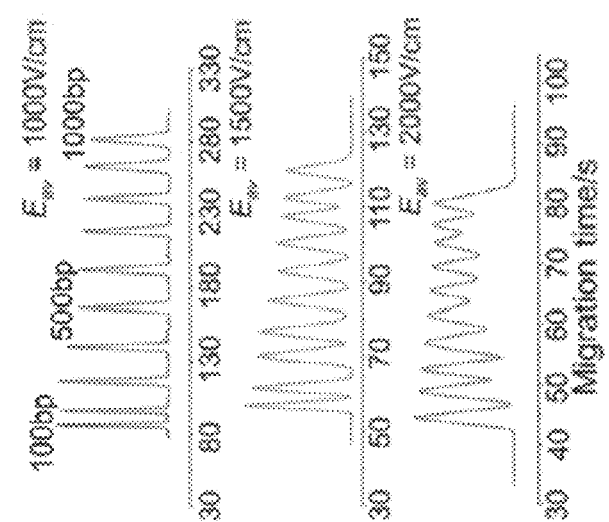
FIG. 7A shows electrophoretic separation of a 100 bp DNA ladder from an artificial sieving structure (unit length $L_u$=4 µm; capillary diameter $d_c$=70 nm; separation channel length $L_s$=2 cm) under three different electric field strengths.
Figure 8B:
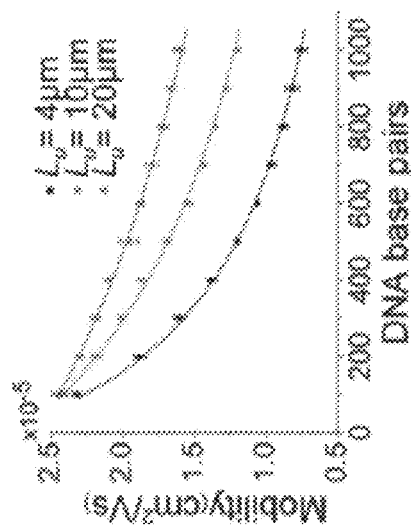
FIG. 8B shows a mobilities as a function of DNA fragment sizes of the 100 bp DNA ladder through the artificial sieving structures of FIG. 8A.
Figure 8C:
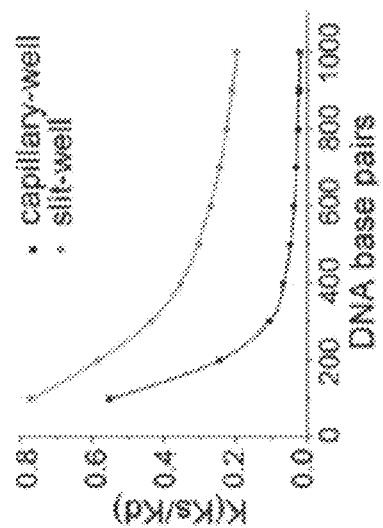
FIG. 8C shows trap times as a function of DNA fragment sizes of the 100 bp DNA ladder through the artificial sieving structures of FIG. 8A.
Figure 8A:
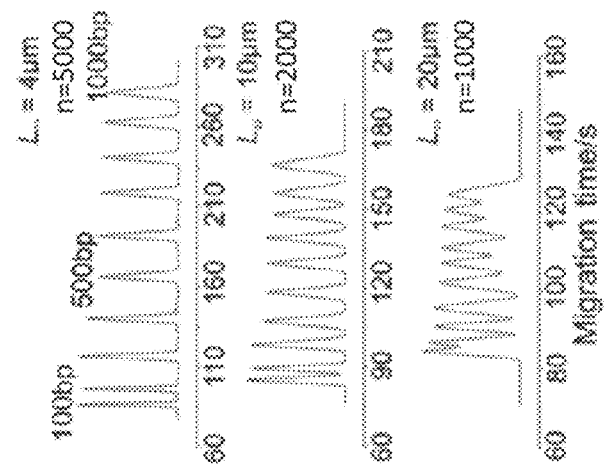
FIG. 8A shows electrophoretic separation of a 100 bp DNA ladder from three different artificial sieving structures ($d_c$=70 nm; $L_s$=2 cm; numbers of motifs n=5000, 2000 and 1000, respectively) under an electric field strength of 1000 V/cm.

FIG. 6A shows a three-dimensional rendering of an area around the interface between a well and a group of capillaries in a well-capillary motif, according to an embodiment. The well and the trenches are etched into an insulator layer so that only the insulator material of the insulator layer is exposed to the interior of the well and the trenches. After etching, no semiconducting or conducting material is exposed. The insulator layer may be on a semiconducting or conducting substrate. Alternatively, the insulator layer is part of a substrate entirely made of the same insulator material of the insulator layer. For example, the substrate may be a glass or quartz substrate. FIG. 6B shows trenches (e.g., with a width greater than 1 micron) are made in an insulator layer, for use as a template for forming the capillaries therein. FIG. 6C shows nonconformal deposition of a film (e.g., doped glass) into the trenches. Doping may lower the melting temperature or glass transition temperature. If the film and the trenches are made of the same base material but the film is doped (or doped more heavily), the film can melt or undergo glass transition without softening the trenches. As the film grows thicker, the film pinches off the top openings of the trenches, thereby enclosing a tubular void therein. FIG. 6D shows reflow of the film during thermal annealing and as a result the transformation of the tubular void into a capillary. The tubular void has a larger diameter than the capillary. Reflow reduces the diameter of the tubular void and transforms it to a capillary. Extending the annealing time reduces the capillary diameter. The arrows indicate the thermal reflow of the film. The well may be etched after the reflow of the film.

The insulator layer may be a low-temperature oxide (LTO) layer. The substrate may be a silicon wafer covered with a 1 µm thick thermal oxide. The insulator layer may be phosphorus-doped glass (phosphosilicate glass (PSG)) or borophosphosilicate glass (BPSG), may have a thickness of 5 µm and may be deposited by plasma-enhanced chemical vapor deposition or low-pressure CVD (LPCVD, at, e.g., 180 mTorr, 420° C.). In the example shown in FIGS. 6A-6D, the trenches are 2 µm wide and 2 µm deep, formed in the insulator layer by conventional photolithography and advanced oxide etching (AOE). Before depositing the film, a thin (e.g., 100 nm) diffusion barrier (e.g., silicon nitride) may be deposited on substrate. The tubular void may be annealed (e.g., at 1000° C. for 1 h) to reflow the insulator layer, during which the tubular void will transform into a capillary. A further annealing step may be performed to reduce the size of the capillary (e.g., to below 100 nm), after the sample-injection cross-junction and wells are fabricated. For example, the capillary may be annealed in a rapid thermal annealing system.

Measurements.

All experiments in this disclosure took place on an epifluorescence microscope (FN1, Nikon) equipped with a 10×/0.3 NA objective lens (Carl Zeiss) and a diode-pumped solid-state laser at 473 nm (LSR473NL, Lasever Inc.) replacing the halogen lamp house to effectively induce fluorescence. Individual fluorescent bands of DNA strands were eluted as a result of electrophoretic separation and captured through a CCD camera (RT3Mono, SPOT) mounted on the microscope. DNA was prestained with intercalating dye SYBR Green (Sigma-Aldrich) at a dye-to-base-pair ratio of 1:2.5 and prepared to a final concentration of 50 µg/mL in 5×TBE electrophoresis buffer (450 mM Tris/borate, 10 mM EDTA (ethylenediaminetetraacetic acid), pH 8.3) containing 1% v/v poly(vinylpyrrolidone) (PVP, MW=10000) to suppress electroosmotic effect. The artificial sieving structure was loaded prior to introducing the DNA sample by placing the electrophoresis buffer in all the reservoirs. Double-stranded DNA (dsDNA) fragments from bacteriophage lambda cI857 Sam7 (λDNA) along with a mixed digest of EcoRI-cut λ-phage DNA (3530-21 226 bp) were all obtained commercially (Sigma-Aldrich), while a 600 bp DNA at the O allele of human ABO blood group gene was amplified by polymerase chain reaction (PCR). The artificial sieving structure is not limited to electrophoresis of these particular DNA samples, which were used here to demonstrate the function of the artificial sieving structure. Injection and separation of a sample plug was realized with electric fields applied through platinum electrodes (Leego Precision Alloy) immersed in the reservoirs from a high-voltage power supply (Tianjin Dongwen Co. Ltd.). Time-series images were analyzed through an image processing software (ImageJ, NIH, Bethesda), and respective electropherograms were generated based on fluorescence intensities acquired from the region of interest (ROI about 2 µm by 2 µm). The particular equipment and reagents were used for demonstration of the function of the artificial sieving structure and are not limiting on the scope of this disclosure.

Results and Discussion

Figure 2A:
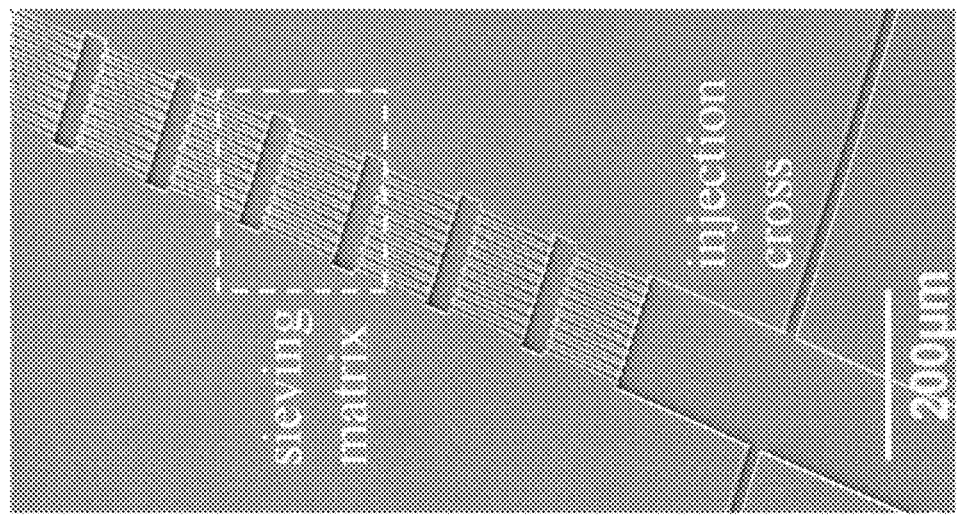
FIG. 2A shows an SEM image of a part of an artificial sieving structure, prior to deposition of the film (scale bar: 200 µm), according to an embodiment.
Figure 2B:
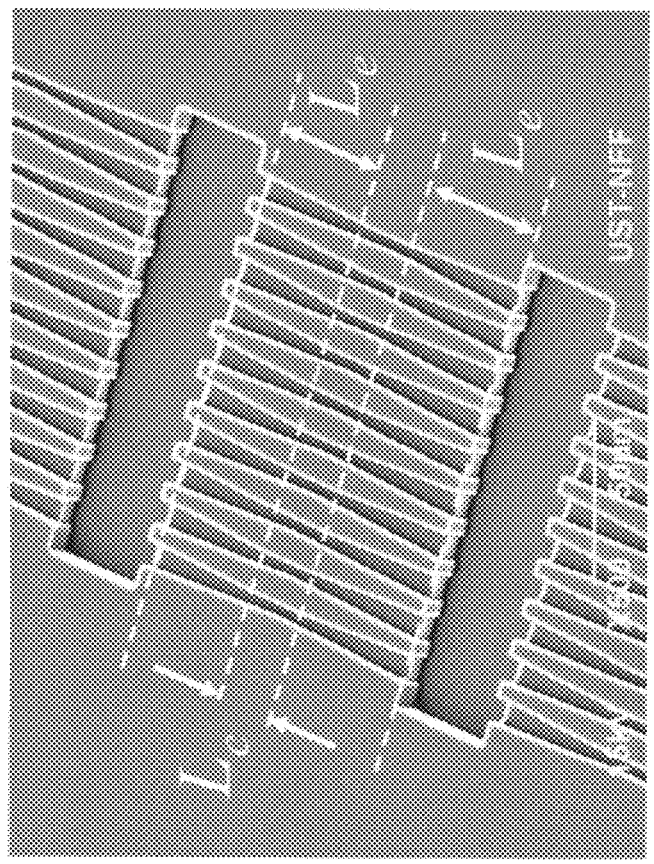
FIG. 2B shows an enlarged SEM image of the portion in the dotted box in FIG. 2A before deposition and thermal reflow of the film (scale bar: 50 µm), according to an embodiment.
Figure 2C:
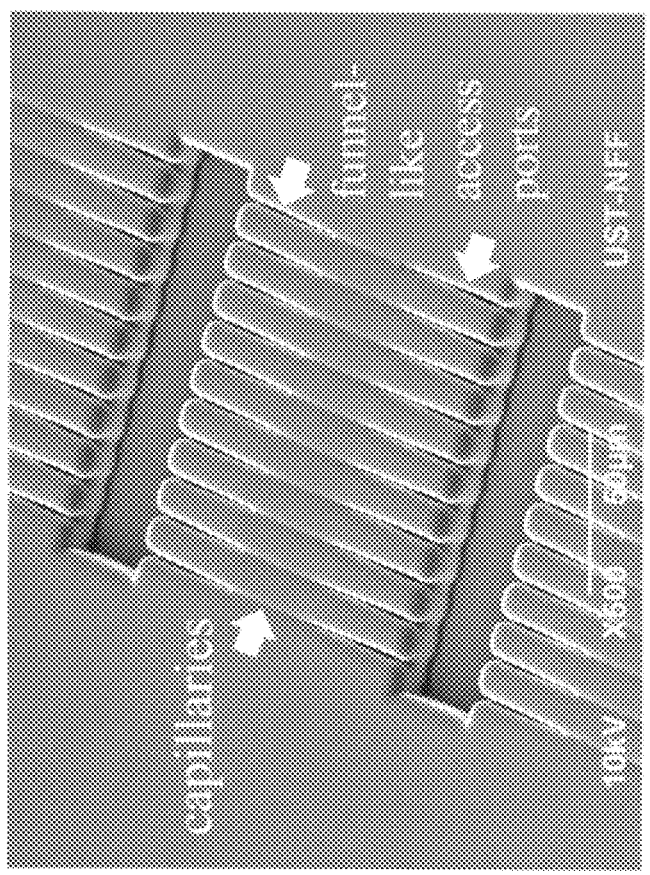
FIG. 2C shows an enlarged SEM image of the portion in the dotted box in FIG. 2A after deposition and thermal reflow of the film (scale bar: 50 µm), according to an embodiment.
Figure 2D:
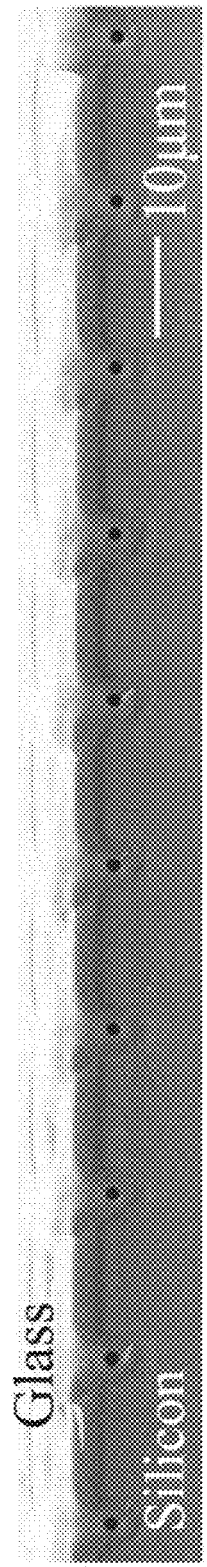
FIG. 2D shows a cross-sectional SEM image of the capillaries (e.g., along the line of AA in FIG. 1A.

Sieve Structure. FIG. 2A shows an SEM image of a portion of the artificial sieving structure, prior to deposition of the film, according to an embodiment. The separation channel can be seen extending from the sample injection cross-junction. The sample can be electrokinetically injected through one of the side channels 20 µm wide and 5 mm long into the separation channel 140 µm wide and 5 mm long. The channel integrates a sieving matrix of 32 (n) well-capillary motifs and offset 200 µm from the sample injection cross-junction. Each motif has a segment of capillaries flanked by a pair of wells 35 µm long and 140 µm wide as depicted in close-up views before and after deposition and thermal reflow of the film (FIG. 2B and FIG. 2C). Each segment of capillaries contains 10 essentially identical nearly cylindrical capillaries. Each of the capillaries has a segment of a uniform width 3.5 µm and length 10 µm ($L_c$). Each of the capillaries has funnel-like ports formed during thermal reflow of the film within diverging trench segments over a length of 50 µm ($L_e$) and terminating at a width (W) of 7 µm. All the wells and channels in this specific example are 13 µm deep, while the trenches are 3.5 µm deep prior to deposition of the film. The depth may vary along with the length of the uniform trench segment ($L_c$). FIG. 2D shows a cross-section of the capillaries. The diameter of the capillaries in this example is about 750 nm, achieved through low-resolution photolithography. The various components of the artificial sieving structure are not limited to the particular dimensions in this example.

Capillary Segment Length. The performance of artificial sieving structure was first evaluated on electrophoretic separation of mixed digests of EcoRI-cut λ-phage DNA (3530-21 226 bp) and compared across three designs nominally identical in all features, including the channel/well depth (23 µm), except the uniform capillary length $L_c$ (10, 100, and 200 µm), and hence the total number of motifs n, cascaded along the 5 mm long separation length (32, 19, and 13). The size of a representative sample DNA plug is shown during a "pinched" injection scheme (FIG. 3A), migrating toward the anode in the capillary-free region of the separation channel (FIG. 3B). FIG. 3C, FIG. 3D and FIG. 3E show electropherograms obtained from these three designs at the detection point approximately 5 mm downstream of the injection cross-junction at an average field of 1.6 kV/cm. As can be seen, through the design with 10 µm long capillaries, the DNA fragments were resolved into two separate bands in less than a minute. With a radius of gyration ($R_g$~345 nm for 21 kbp) smaller than the capillary diameter (750 nm in this example), the fragments elute in ascending order of chain length on the basis of Ogston sieving. Accordingly, the peak eluted last belongs to the longest chain length (21 kbp), while the faster peak contains all the smaller fragments that could not be resolved within the given separation length (3.5, 4.8, 5.6, 5.8, and 7.4 kbp). This has been verified also through experiments whereby sample plugs of homogeneous chains were independently electrophoresed through the artificial sieving structure and the smaller chain size (600 bp) was repeatedly found eluting out earlier than intact λ-DNA (48.5 kbp). From the electropherograms in FIG. 3C, FIG. 3D and FIG. 3E, it is noticeable that the resolving power deteriorates, as the capillaries get longer and a less number of units can be packed along the separation channel of a given length. For each design, the resolution, $R_s=2\Delta t/(W_1+W_2)$, which is the distance between the two peaks scaled by their average width at base, is listed in Table 1. A 10-fold increase in the capillary length $L_c$ to 100 µm reduces the resolution below a critical value of 1, while a further increase to 200 µm makes the two peaks barely resolvable ($R_s=0.79$). Overall, the cumulative capillary length that the DNA fragments have to go through is increased from 310 to 2600 µm while the number of units is reduced from 32 to 13. This suggests that DNA sieving mainly occurs at the capillary-well interface (entropic barrier) rather than capillary interior. Exemplary values for the theoretical plate number $N_t$ of the capillary matrix are in the order of $10^3$ and also decline with the increased capillary length $L_c$ as listed in Table 1. Table 1. Device Specifications and Separation Metrics Pertaining to the Plots (FIG. 3C, FIG. 3D and FIG. 3E)

| Specifications | | | Performance | |
| --- | --- | --- | --- | --- |
| $L_c$ (µm) | n | n × $L_c$ (µm) | $R_s$ | $N_t$ (×$10^3$) |
| 10 | 32 | 310 | 1.34 | 2.39[a] |
| 100 | 19 | 1900 | 0.96 | 1.40[a] |
| 200 | 13 | 2600 | 0.79 | 1.43[a] |

[a] According to the peak representative of 21 kbp chains in FIG. 3C, FIG. 3D and FIG. 3E.

Characteristic Threshold Voltage. According to an embodiment, the artificial sieving structures may have a threshold voltage greater than those reported for the slit-well motifs. The threshold voltage is the voltage below which substantially no samples (e.g., <5%) cannot be driven through the artificial sieving structures. For example, the artificial sieving structures described above (FIGS. 3A-3E) have a threshold voltage of about 800 V. This high threshold voltage could be mainly attributed to the fact that majority of the applied voltage falls across the capillaries, given their extremely high electrical resistance leaving the voltage across and the electric field in the wells fairly low (<3 V/cm for a voltage below 800 V). Such low electric field (about 3 V/cm) may be sufficient in the slit-well structure of a comparable separation length to drive the sample through and may be generated in the slit-well structure with merely tens of volts. The electric field in the capillaries (e.g., about 2 kV/cm at 800 V) may be at least an order of magnitude higher than that in the slits (about 150 V/cm at 120 V applied over 15 mm).

Figure 4A:
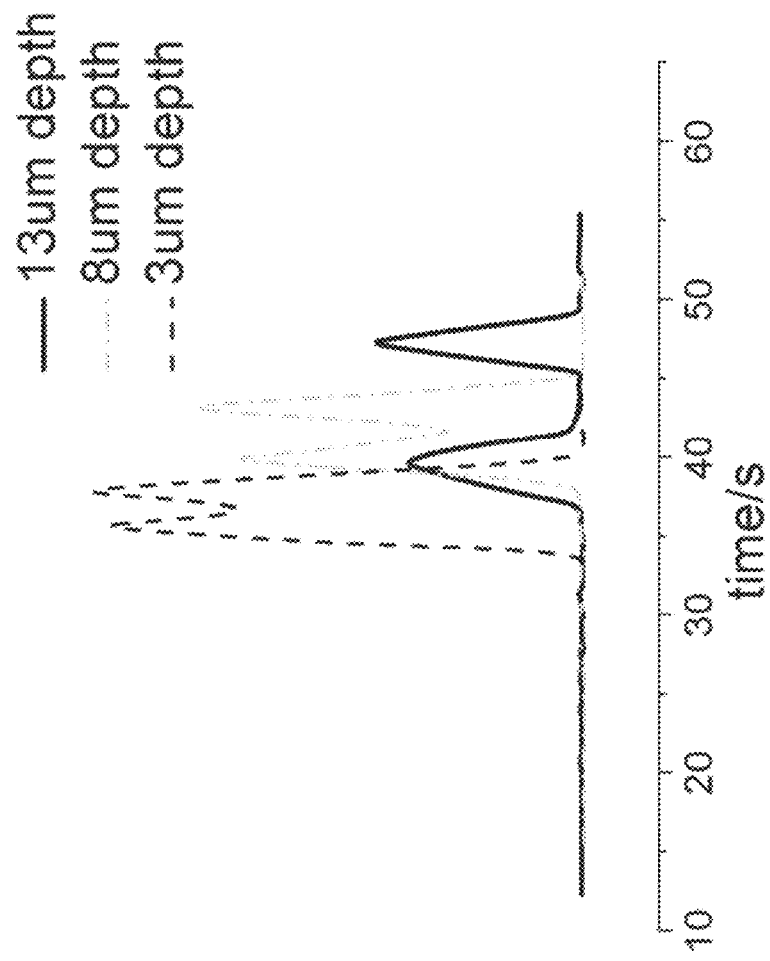
FIG. 4A shows electropherograms from the artificial sieving structures that are identical except with varying channel/well depth and subjected to a fixed electric field strength at 1 kV/cm ($L_c$=10 µm and n=32 along the separation length of 5 mm), where n is the number of capillary-well motifs in along the separation channel of the artificial sieving structure.

Well Depth. Local field intensity at the steps (i.e. interfaces between a well and its neighboring capillaries) can be further enhanced through a reduced well depth so as to attain a lower threshold voltage. Threshold voltage for the band launching, for instance, across the designs with 10 μm long capillaries, 5 mm long separation channel, and a well depth of 23, 13, 8, and 3 μm was identified to be near 800, 400, 300, and 150 V, respectively. With a well depth of 13 μm, 500 V was sufficient to launch DNA chains into two separate bands, as shown in FIG. 4A, slightly better in $R_s$=1.98 and $N_t$=3.4×10$^3$ than through the same design with a well depth of 23 μm. A slight increase in the migration speed was also noticed. A further reduction in the well depth continued to increase the migration speed and enhance the theoretical plate number but also deteriorated the resolution. This is in contrast with the slit-well design where a reduced well depth caused an increase in the separation selectivity during entropic trapping regime owing to the subsequent reduction in the slit electric field and thus the escape probability of the molecules. In the artificial sieving structures, however, the electric field in the capillary hardly changes (<0.5% at 1.4 kV/cm) while the electric field in the wells proportionally increases from 2 to 15 V/cm in response to about 7-fold reduction in the well depth. While such field increase led to a slightly faster migration speed, it compromised separation selectivity because of its more profound impact on the large molecules (21 kbp) than those smaller. This rather concurs with the field-dependent electrophoretic mobility of molecules observed with the slit-well configuration during the Ogston sieving regime, which reportedly influences the larger molecules more.

Figure 4B:
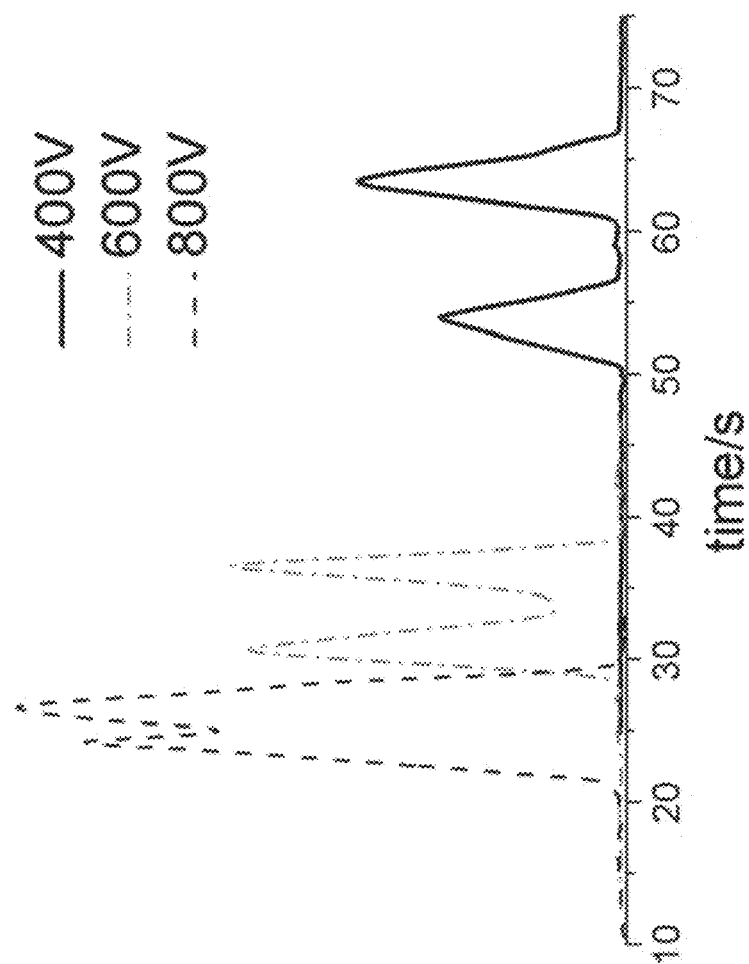
FIG. 4B shows electropherograms from the artificial sieving structures that are identical with a fixed channel/well depth of 13 µm but subjected to varying electric field strengths ($L_c$=10 µm and n=32 along the separation length of 5 mm)

Separation Voltage. A similar trend was also noticed when the electric field increase originated from a surge in voltage intensity provided that the voltage applied across the separation channel was above the threshold voltage. For instance, on the design with a fixed well depth of 13 μm, both the peaks increased migration rate by about 1.75-fold, responding more or less equally to a level rise from 400 to 600 V (FIG. 4B). From 600 to 800 V, a somewhat higher mobility, however, was unveiled by the large chains (21 kbp). This might be explained by that larger chains may have a higher threshold voltage. It should be noted that the projected field strengths within the wells, 4 and 5.4 V/cm at 600 and 800 V, respectively, remain far below 15 V/cm, the field strength reachable at a lesser voltage (500 V) when the well depth is 3 μm (FIG. 4A). Therefore, the dramatic increase observed in the overall migration rate must result primarily from an increased capillary electric field (2.3 kV/cm at 800 V) typically about 1.6-fold of those reported in FIG. 4A.

Figure 5A:
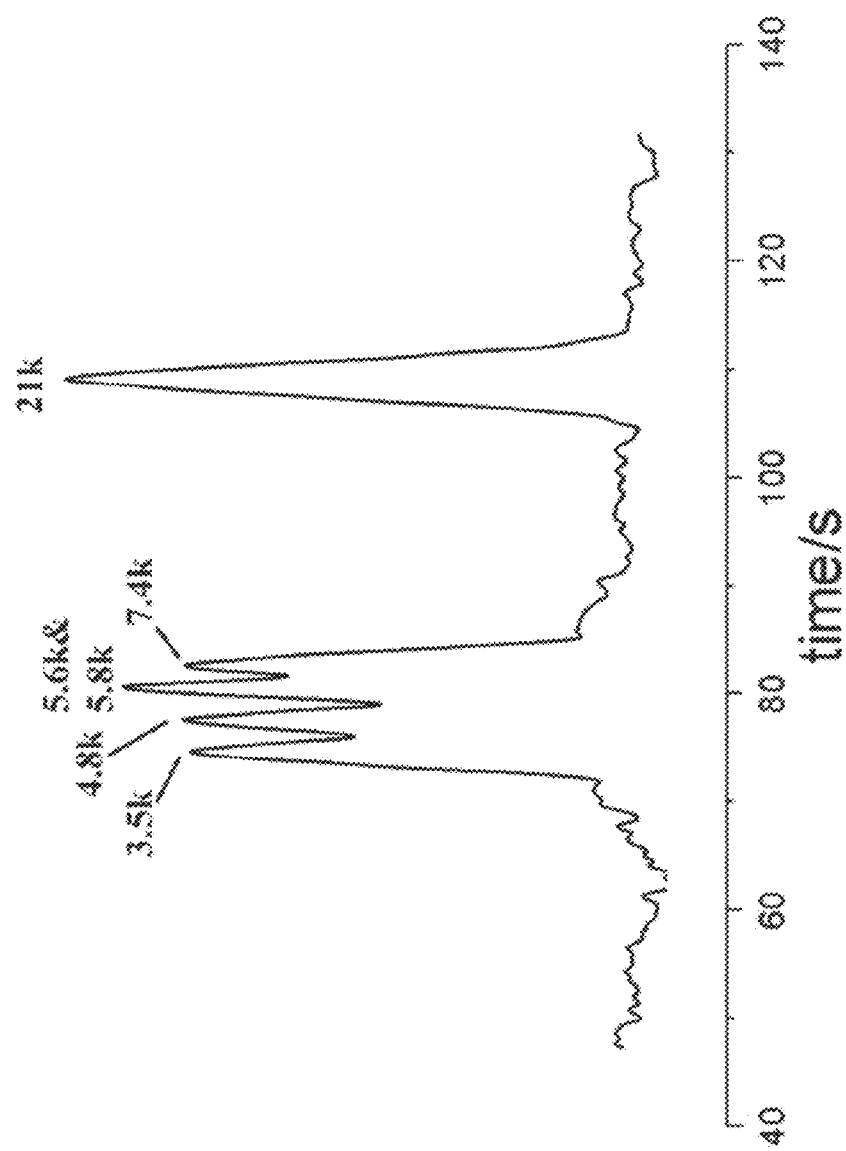
FIG. 5A shows an electropherogram obtained at the end of a 20 mm long separation channel having n=128, $L_c$=10 µm, and the channel/well depth of 13 µm (separation electric field strength: 800 V/cm)

Separation Length. To further resolve the smaller fragments within the first-eluted band, the separation length was increased by a factor of 4 on the design with 10 μm long capillaries and a fixed well depth of 13 μm. This led to a 4-fold increase in the number of capillary units to n=128 cascaded along the separation length 20 mm. At the threshold field, 800 V/cm, the smaller fragments were successfully separated from the larger chains (21 kbp) being completely resolved within only 4 min as shown in FIG. 5A. The bands 5.6 and 5.8 kbp, although being very close, were still resolvable ($R_s$=1.23) within the extended length. Also, an order of magnitude increase in the theoretical plate numbers 2.3-6×10$^4$ plates (1.2-3×10$^6$ plates/m) was noted in comparison to those in FIG. 3B. These values are on par with those from the state-of-the-art sieving matrixes at comparable lengths and yet achieved here at a fraction of their time. This can be attributed to that the equilibrium-sieving mode can be sustained in the structures disclosed herein at a much greater average field. The short fragments were observed to resolve, although not fully, even at the separation length of 10 mm (n=64).

Figure 5B:
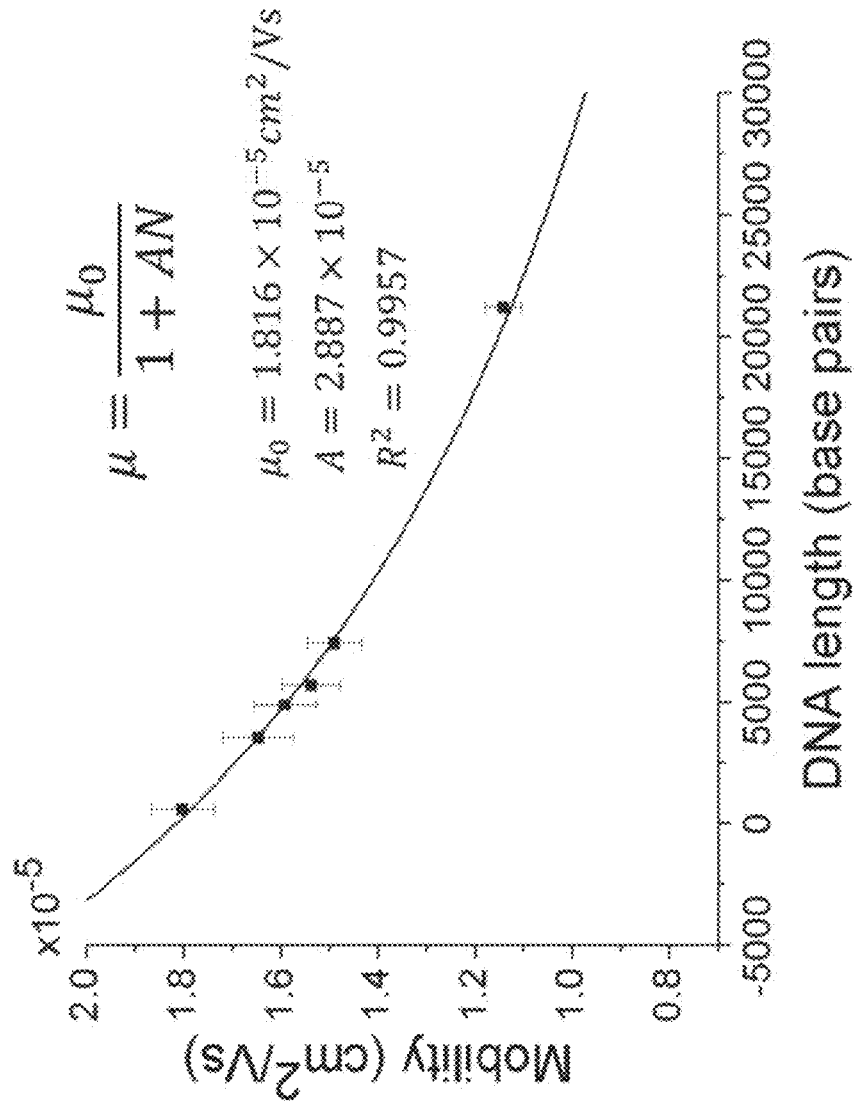
FIG. 5B and FIG. 5C show DNA mobility and the mean trapping time $\tau_{trap}$ in the same matrix as a function of the chain length (600 bp to 21 kbp), where the error bars in FIG. 5B indicate the standard errors of the respective mean values (the symbols) for five repetitious runs on the same device, and the symbols in FIG. 5C indicate the values obtained from Eq. (1) using the measured average mobility and $\mu_{max}$ (the curve is based on Eq. 2 with the fitting parameter $\alpha=2.5\times10^5$ $V^2s/(m^2bp)$)

Electrophoretic Mobility. FIG. 5B reveals the mobility data derived from the DNA band elution time, the migration distance, and the applied electric field. The data also includes the mobility value for the smaller chains (600 bp) independently electrophoresed in the same design through which EcoRI-cut λ-DNA fragments were separated. Fitting to a model where the mobility $\mu=\mu_{max}/(1+AN)$ is expressed in terms of the number of base pairs N and two fitting parameters $\mu_{max}$ and A showed excellent agreement for a specific combination of $\mu_{max}$=1.82×10$^{-5}$ cm$^2$/(V s) and A=3.5×10$^{-5}$ (R$^2$=0.993). The former is the maximum sieving-free mobility inside the design, whereas the latter is inversely related to the average electric field $E_{av}$ along with the sieve geometry including the unit length $L_u$, and partition coefficient K according to the equilibrium partitioning theory and Kramer's theory (see below). It should be noted that the slope of the mobility curve dμ/dN is an increasing function of A and rather significant as it determines the size selectivity of the design. A greater size selectivity occurs with a large A and thus requires that the term $L_u E_{av} K$ be kept at a minimum.

Figure 5C:
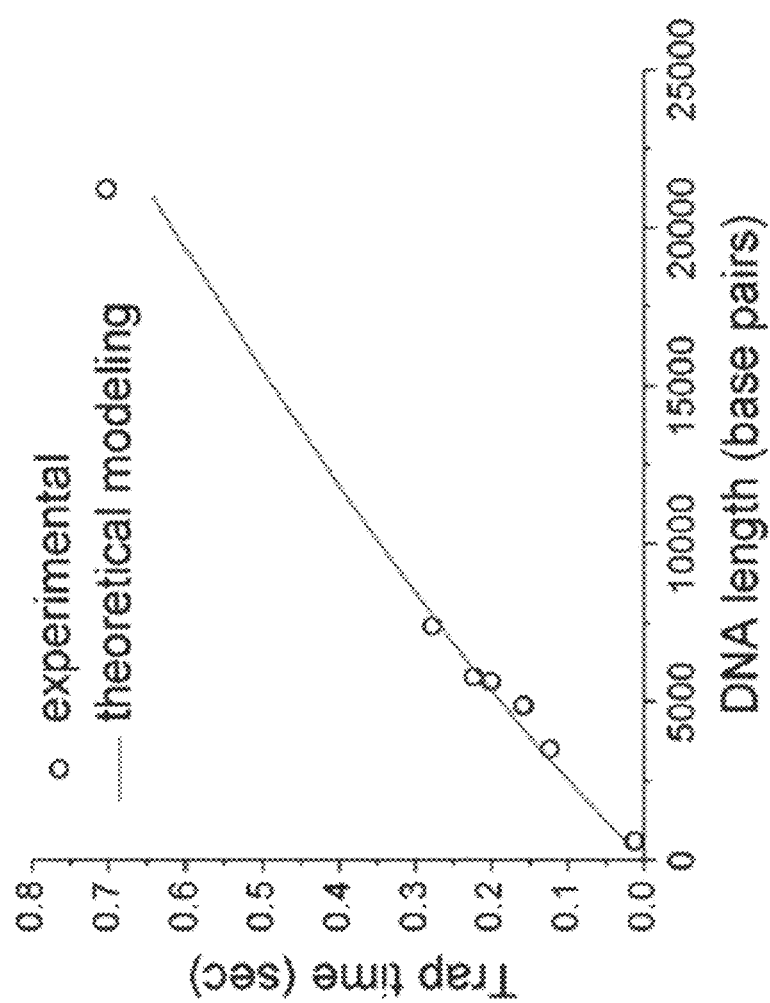
Figure 5D:
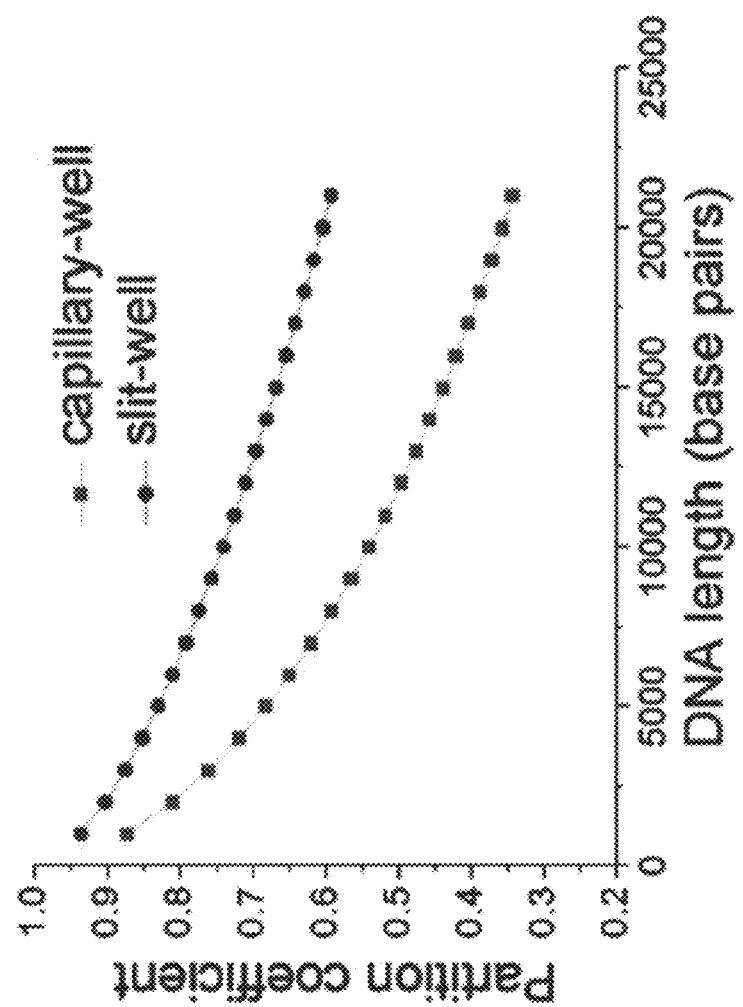
FIG. 5D show partition coefficient values as a function of the size of the chain length calculated for the capillary matrix and similar slit-well motif.

Mean Trapping Time. The DNA fragments migrating through the capillary matrix spends on average a finite lifetime at a capillary entrance (entropic barrier). The mean trapping time $\tau_{trap}$ can be inferred from the experimental mobility values through the following relation:

$$\mu = \frac{\mu_{max}}{1 + \tau_{trap}/\tau_m} \quad (1)$$

where $\tau_m = L_u/\mu_{max} E_{av}$ refers to the drift time of the molecules between the consecutive traps. FIG. 5C shows the values calculated based on the mean experimental mobility and compares them to a curve obtained from the kinetic model based upon the equilibrium partitioning theory and Kramer's rate theory:

$$\tau_{trap} = \frac{\alpha N}{E_{av}^2 K} e^{-\varepsilon} \quad (2)$$

where α is the fitting parameter, K is the partition coefficient of the capillary-well matrix described in FIG. 5D, and $\epsilon=\Delta W/k_B T$ is the reduced potential with $\Delta W$ being the electrical potential energy drop in the translation of molecules over the entropic barrier along the field direction, $k_B$ being the Boltzmann's constant, and T being the absolute temperature. The electrical potential energy drop can be approximated as $$\Delta W = NqE_w d_r \quad (3)$$

where q is the effective charge per base pairs, $2.49 \times 10^{-21}$ C/bp, $E_w$ is the electric field within the wells, and $d_r = (Dt_w)^{1/2}$ is the transition region radius given by the characteristic diffusion length of the molecules (D~$N^{-0.6}$ being the diffusion coefficient of the molecules and $t_w = L_w/\mu_{max}E_{av}$ being the average time it takes for the molecules to cross the well length $L_w$).

The theoretical curve agrees well with the experimentally derived $\tau_{trap}$ values (FIG. 5C). The slight deviations could be attributed to the non-negligible internal conformations and rotational states of the coiled chains in the kinetics of overcoming the entropic barriers. It should be highlighted that Eqs. (1) and (2) can be combined to obtain the mobility fitting parameter: $A=\mu_{max}\alpha e^{-\epsilon}/L_u E_{av} K$.

In Comparison to the Slit-Well Motif. Ogston sieving mechanism in the slit-well structure breaks down at high fields (100 V/cm) with an inevitable loss of resolution for rod-like DNA. Lowering the field could recover the selectivity (A) but would also cause a great delay in migration time; sieving 100 bp DNA ladder takes about 3 h to complete at about 26 V/cm. Considering the size of the chains separated here (several thousand base pairs) and the critical sieve dimension (750 nm), a direct comparison is made with theoretical predictions from Eqs. (1) and (2) for a similar slit-well model upon replacing the capillary segments with slits 750 nm deep, 140 μm wide, and 110 μm long in the design associated with FIGS. 5A-5D. In such a slit-well model subjected to a high field strength ($E_{av}$=800 V/cm), the mean trapping time $\tau_{trap}$ is found to be extremely small in the order of hundreds of nanoseconds, negligible in comparison to $\tau_m \approx 1$ s. Thus, the mobility is nearly constant, $\mu \approx \mu_{max}$, independent of N, implying no separation (the size selectivity $A=4\times10^{-11}$).

The mean trapping time of the chains by the slits is suggested to be 6 orders of magnitude shorter than those by the capillaries (hundreds of milliseconds). This cannot be simply explained by the partition coefficient K. As shown in FIG. 5D, K is expectedly smaller in the capillary-well motif than in the slit-well motif and decays faster with the chain length. Yet, the deviation in K values does not grow apart more than an order of magnitude even for the largest chains. The fitting parameter $\alpha$ for the two geometries is not expected to vary greatly as it is predominantly determined by the diffusivity of the chains. The exponential term $e^{-\epsilon}$, however, renders variations in the reduced potential ($\epsilon=\Delta W/k_B T$) far more significant. In the capillary matrix, $\epsilon$ remains less than 1 ($\epsilon$~0.5) based on $\Delta W \approx k_B T$, whereas in the slit-well configuration $\Delta W$ is at least an order of magnitude larger than $k_B T$, hence, $\epsilon > 10$. Such variation in $\epsilon$ is sufficient to account for the suggested differences in $\tau_{trap}$. A higher $\Delta W$ prevails in the slit-well motif than in the capillary-well matrix as the field strength $E_w$ in the former quickly climbs up with the applied voltage (64 V/cm as opposed to 2.6 V/cm).

Simulations and experiments performed on the slit-well design, however, revealed a nonequilibrium sieving mode beyond the Ogston breakdown where higher fields help separation recover but with a reversed elution order of bands and a speed 1-2 orders of magnitude faster than with Ogston sieving at lower fields. Still, the selectivity is compromised as compared to the Ogston sieving regime. A highly restrictive sieve structure, like the capillaries here, sustains differential migration of chains at higher fields without compromising the selectivity or Ogston equilibrium, thereby achieving a fast separation. Inside a capillary, the configurational freedom of molecules is limited to a quasi-one-dimensional space (smaller partition coefficient, K, and thus greater entropic energy barrier $-k_B T \ln K$). More importantly, the capillaries impose a higher electrical resistance, limiting the field strength inside the wells to a small fraction (<1%) of the average field even at high operating voltages applied for a fast separation. This ensures that the driving electrical potential energies commensurate with the entropic barriers such that the separation takes place near equilibrium for an optimum resolving power.

The artificial sieve structures disclosed herein with a fast sieving characteristic may lead to future integrated nucleic acid analyses systems that are compact, fast, and more practical. The structure could be further optimized for a range of applications. For instance, the capillary diameter can be tailored through anneal time and temperature for sieving shorter or longer DNA chains as well as specific proteins. The capillary diameters evaluated (150 nm or greater) in our design with λ-DNA ($R_g \approx 520$ nm) revealed the crossover from Ogston-like sieving to entropic trapping. The capillaries (with diameters as small as 70 nm), owing to their confining nature, impose substantially greater entropic barriers on molecules than less resistive slits or pillars do at their onsets. Thus, driving molecules over these steep energy barriers may use electric fields much stronger than the fields used in devices with slits or pillars, and this leads to an effective size-based separation of molecules. The artificial sieving structures disclosed herein show good resolving power over a broad range of field strengths.

What is claimed is:

1. A device for electrophoresis comprising:
   a semiconducting, insulating, or conducting substrate;
   a separation channel in the substrate; and
   a plurality of capillary-well motifs cascading along the separation channel, each of the plurality of capillary-well motifs comprising a well and a plurality of non-intersecting capillaries, wherein
   the capillaries are downstream from the well and fluidly connected thereto,
   an interface between the well and the capillaries comprises a step profile, and
   wherein the capillaries have a diameter of 750 nm or less.

2. The device of claim 1, wherein the well has a greater dimension in a direction perpendicular to a flow of the separation channel than that of the capillaries.

3. The device of claim 1, wherein the capillaries comprise a center section of essentially uniform cross-sectional area.

4. The device of claim 3, wherein the capillaries comprise fluid access ports with a greater cross-sectional area than the center section.

5. The device of claim 1, where the wells of the plurality of capillary-well motifs are essentially identical in their dimensions.

6. The device of claim 1, where the capillaries of the plurality of capillary-well motifs are essentially identical in their dimensions.

7. The device of claim 1, where the wet is positioned perpendicularly to the capillaries.

8. The device of claim 1, further comprising a sample channel and one or more reservoirs.

9. The device of claim 1, wherein the plurality of capillary-well motifs comprises at least 10 capillary-well motifs.

10. The device of claim 1, wherein the plurality of capillary-well motifs comprises at least 100 capillary-well motifs.

11. The device of claim 1, wherein the plurality of non-intersecting capillaries comprises 10 or more capillaries.

12. The device of claim 1, wherein the plurality of non-intersecting capillaries has a length of 10 microns or more.

13. The device of claim 1, wherein the well has a depth of microns or more.

14. The device of claim 3, wherein the center section is buried.

15. A method of forming a device, the method comprising:
   obtaining a semiconducting, insulating, or conducting substrate comprising an insulator layer of an insulator material;
   forming a plurality of trenches in the insulator layer so that only the insulator material is exposed to an interior of the plurality of trenches;
   nonconformally depositing a film into the plurality of trenches until the film pinches off top openings of the trenches and forms a tubular void therein;
   transforming the tubular void into a capillary by annealing the film; and
   forming a well in the insulator layer so that only the insulator material is exposed to an interior of the well,
   wherein the insulator material is undoped or has a lighter doping than the film.

16. The method of claim 15, further comprising reducing a size of the capillary by annealing the capillary.

17. The method of claim 15, wherein the insulator material is an oxide.

18. The method of claim 15, wherein the substrate is made of the insulator material.

19. The method of claim 15, wherein the substrate is a glass or quartz substrate.

20. The method of claim 15, wherein the insulator material is silicate glass (USG), spin-on-glass (SOG), low-temperature oxide (LTO), high-temperature oxide (HTO), thermally grown oxide, or oxide based on tetraethylorthosilicate (TEOS).

21. The method of claim 15, further comprising depositing a diffusion barrier.

22. The method of claim 15, wherein the capillary has a diameter of 750 nm or less.

23. The method of claim 15, wherein the film is doped glass.

24. The method of claim 23, wherein the film is phosphorus-doped glass (PSG) or borophosphosilicate glass (BPSG).

25. A device for electrophoresis comprising:
   a semiconducting, insulating, or conducting substrate comprising an insulator layer of an undoped or slightly doped insulator material;
   a separation channel in the substrate; and
   a plurality of capillary-well motifs cascading along the separation channel, each of the plurality of capillary-well motifs comprising a well and a plurality of non-intersecting capillaries, wherein
   the capillaries are downstream from the well and fluidly connected thereto,
   an interface between the well and the capillaries comprises a step profile, and
   wherein the capillaries have a diameter of 750 nm or less.

* * * * *